(12) United States Patent
Finberg

(10) Patent No.: US 12,011,383 B1
(45) Date of Patent: Jun. 18, 2024

(54) APPARATUS AND METHODS FOR MAINTAINING A SIDE-SLEEPING POSITION

(71) Applicant: Stephen Finberg, Paradise Valley, AZ (US)

(72) Inventor: Stephen Finberg, Paradise Valley, AZ (US)

( * ) Notice: Subject to any disclaimer, the term of this patent is extended or adjusted under 35 U.S.C. 154(b) by 0 days.

(21) Appl. No.: 18/367,448

(22) Filed: Sep. 12, 2023

(51) Int. Cl.
*A61F 5/37* (2006.01)
*A61F 5/56* (2006.01)

(52) U.S. Cl.
CPC .............. *A61F 5/3776* (2013.01); *A61F 5/56* (2013.01)

(58) Field of Classification Search
CPC ........ A61F 5/37; A61F 5/3761; A61F 5/3769; A61F 5/3776; A61F 5/3784; A61F 5/56; A61G 7/001; A61G 7/00526; A61G 7/075
USPC ......................................................... 128/871
See application file for complete search history.

(56) References Cited

U.S. PATENT DOCUMENTS

| | | |
|---|---|---|
| 1,502,276 A | 7/1924 | Siebert |
| 2,215,454 A | 9/1940 | Condit |
| 2,679,842 A | 6/1954 | Irwin |
| 3,098,479 A | 7/1963 | Storey |
| 3,474,781 A | 10/1969 | Gaylord |
| 3,535,718 A | 10/1970 | Murcott |
| 5,069,229 A * | 12/1991 | Kurth ................. A61G 13/1245 128/877 |
| 7,874,032 B2 | 1/2011 | North |
| 8,429,775 B2 | 4/2013 | North |
| 8,602,032 B2 * | 12/2013 | Goldsmith ............ A61F 5/3776 128/876 |
| 9,585,499 B2 | 3/2017 | North |
| 10,842,696 B1 * | 11/2020 | Wolpe ................ A63B 21/0552 |
| 2014/0041123 A1 | 2/2014 | North |
| 2015/0335507 A1 | 11/2015 | Emmons |
| 2016/0051430 A1 | 2/2016 | Bader |
| 2017/0172308 A1 | 6/2017 | North |
| 2019/0380862 A1 * | 12/2019 | Ferdman ............... A61F 5/3776 |
| 2022/0047228 A1 | 2/2022 | Hull |

* cited by examiner

*Primary Examiner* — Keri J Nelson
(74) *Attorney, Agent, or Firm* — Louis J. Hoffman; David S. Alavi

(57) ABSTRACT

A limb restraint includes a flexible limb sleeve and a strap. The limb sleeve permits a sleeper to insert or remove a limb into or out of the sleeve, intentionally while awake, yet inhibits unintentional removal of the limb from the sleeve by the sleeper while sleeping. The strap connects the limb sleeve to a mattress or bedframe so that the limb sleeve is in front of the sleeper while in a side-sleeping position, and with an upward-side limb of the sleeper inserted into the limb sleeve, so that the limb restraint maintains the sleeper in the side-sleeping position while asleep.

19 Claims, 7 Drawing Sheets

APPARATUS AND METHODS FOR MAINTAINING A SIDE-SLEEPING POSITION

FIELD OF THE INVENTION

The field of the present invention relates to maintaining a side-sleeping position. In particular, limb restraints and methods for their use are disclosed for maintaining a sleeper in a side-sleeping position.

BACKGROUND

A variety of devices exist for restraining or limiting movement of a person on a bed. Such devices can be deployed for a variety of reasons, e.g., fall prevention or involuntary restraint. In some cases the device is attached to the bed in a way that at least partly interferes with movement of the person on the bed, but is not attached to the person. A few examples of such arrangements are disclosed in U.S. Pat. No. 7,874,032 and US 2015/0335507. In some other cases the device is attached to the person to interfere with movement of the person, but is not attached to the bed. A few examples of such arrangements are disclosed in U.S. Pat. Nos. 8,429,775 and 9,585,499. In still other cases, the device is attached to both the person and the bed, typically for the purpose of involuntarily restraining a person on the bed, such as a patient who should not move or a prisoner. A few examples of such arrangements are disclosed in U.S. Pat. Nos. 2,215,454, 2,679,842, 3,098,479, 3,474,781, and 3,535,718.

For some sleepers, breathing issues such as snoring or positional sleep apnea (or both) can vary considerably in intensity depending on whether the sleeper is sleeping on his or her back or side. For many people, sleeping on one's back tends to increase snoring or positional sleep apnea, while sleeping on one's side tends to reduce snoring or positional sleep apnea. Some known devices are intended to maintain a sleeper in a side-sleeping position, to reduce snoring or positional sleep apnea or both. Such devices do not tend to attach to both the person and the bed. A few examples of such arrangements are disclosed in U.S. Pat. Nos. 7,874,032, 8,429,775, 9,585,499, and US 2015/0335507 (noted above).

SUMMARY

A method for maintaining a sleeper in a side-sleeping position can include: (a) securing a limb restraint to a mattress, or to a bedframe supporting the mattress, and (b) inserting a limb of the sleeper into a flexible limb sleeve of the limb restraint while the sleeper lies on the mattress in a side-sleeping position, with the limb inserted into the limb sleeve being an upward-side limb of the sleeper while in the side-sleeping position. The limb restraint includes the flexible limb sleeve and a strap arranged to connect the limb sleeve to the mattress or bedframe. The limb restraint can be secured in a position so that the limb sleeve is in front of the sleeper while sleeping on the mattress in the side-sleeping position.

A limb restraint can include (a) a flexible limb sleeve and (b) a strap. The flexible limb sleeve is sized, shaped, and structurally arranged (i) so as to permit a limb of the sleeper to be intentionally inserted into or removed from the sleeve by the sleeper while awake, and (ii) so as to inhibit unintentional removal of the limb from the sleeve by the sleeper while sleeping. The strap is connected to the limb sleeve and couplable to a mattress, or to a bedframe supporting the mattress. The connection between the strap and the limb sleeve is positioned so that (i) the limb sleeve is in front of the sleeper while sleeping on the mattress in a side-sleeping position, and (ii) the limb sleeve is positioned to receive an upward-side limb of the sleeper.

Objects and advantages pertaining to maintaining a side-sleeping position may become apparent upon referring to the example embodiments illustrated in the drawings and disclosed in the following written description or appended claims.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Figure 1:
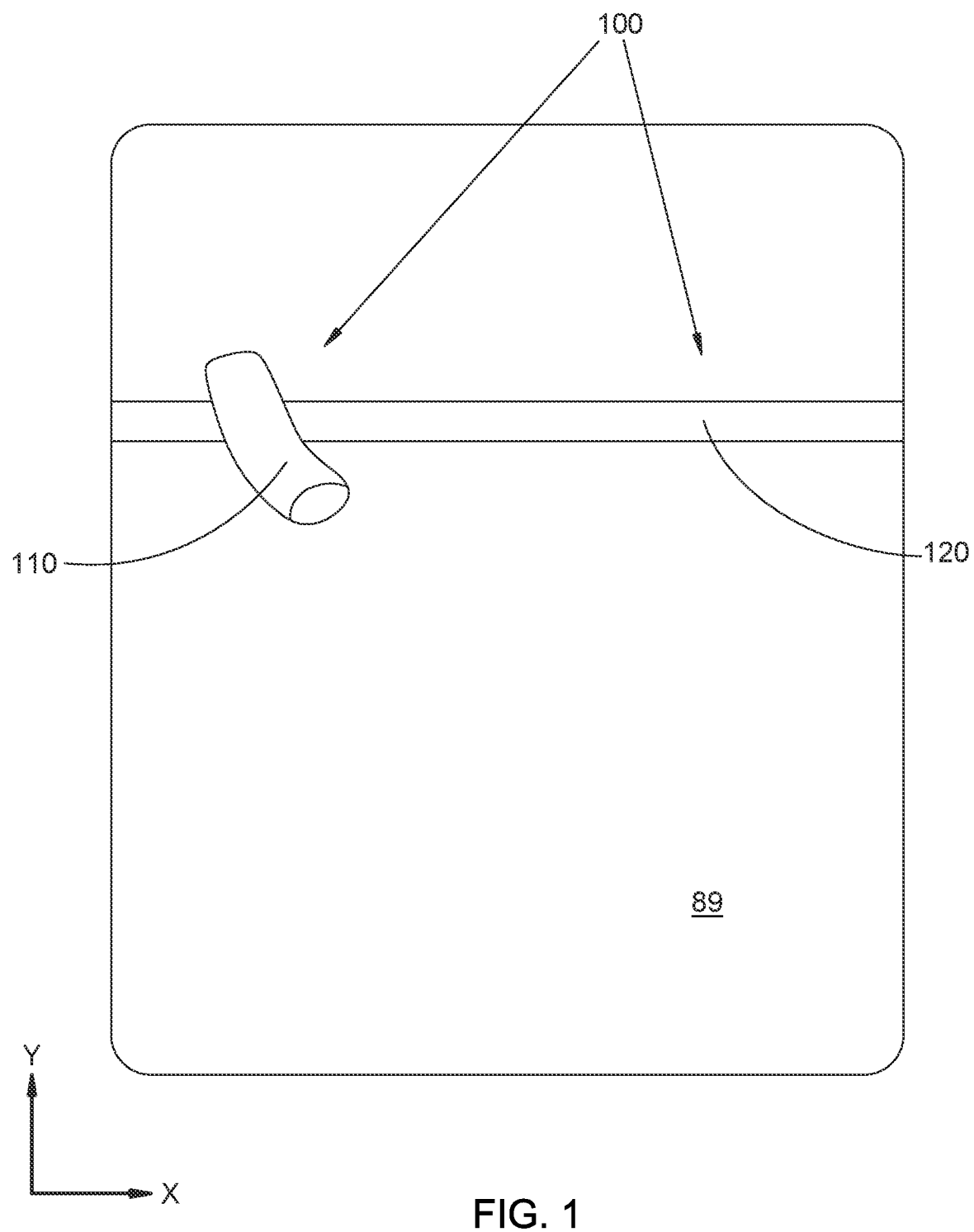
FIG. 1 illustrates schematically an example of a limb restraint having a transverse strap and being positioned for receiving a side-sleeper's arm.
Figure 2:
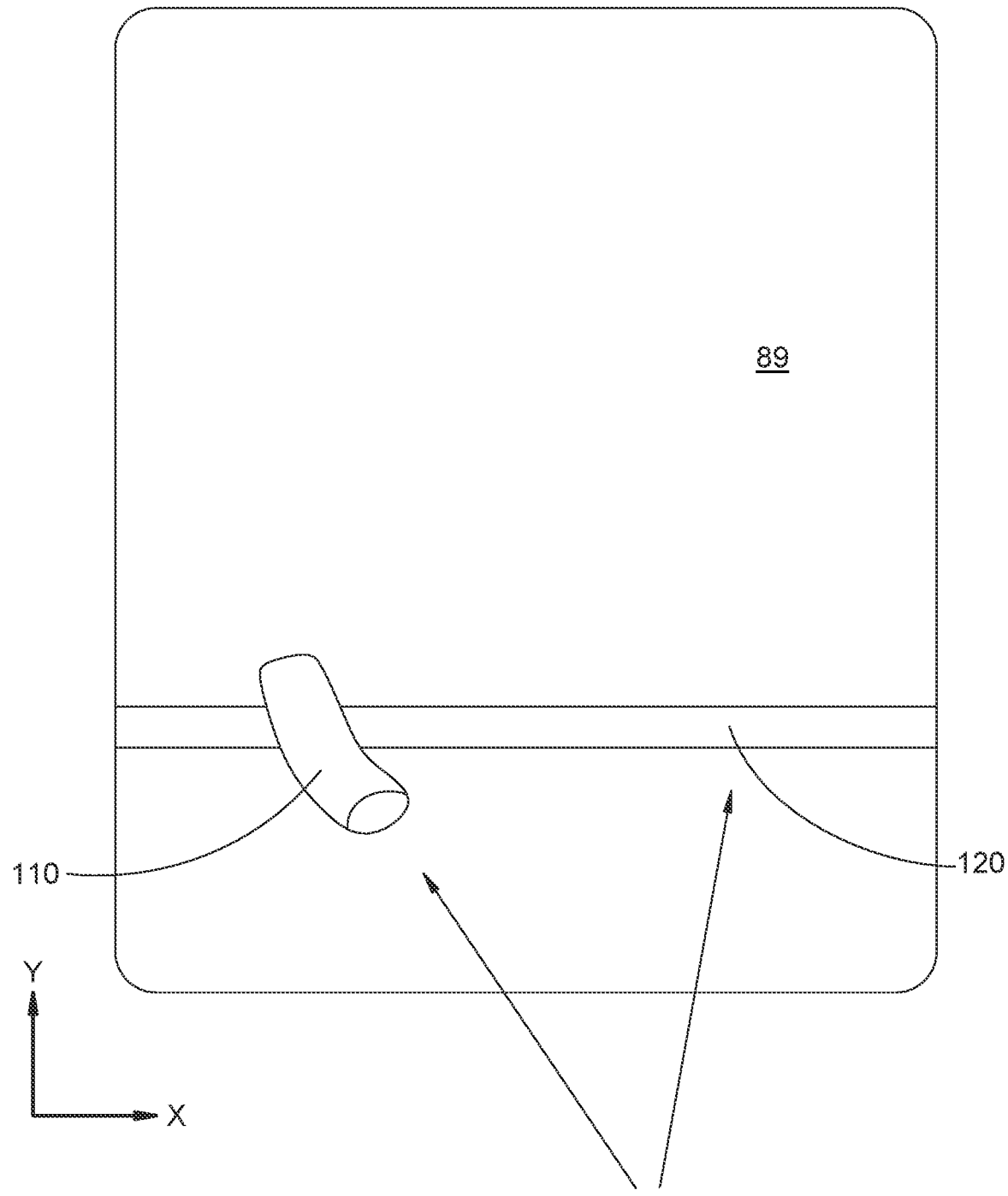
FIG. 2 illustrates schematically an example of a limb restraint having a transverse strap and being positioned for receiving a side-sleeper's leg.
Figure 3:
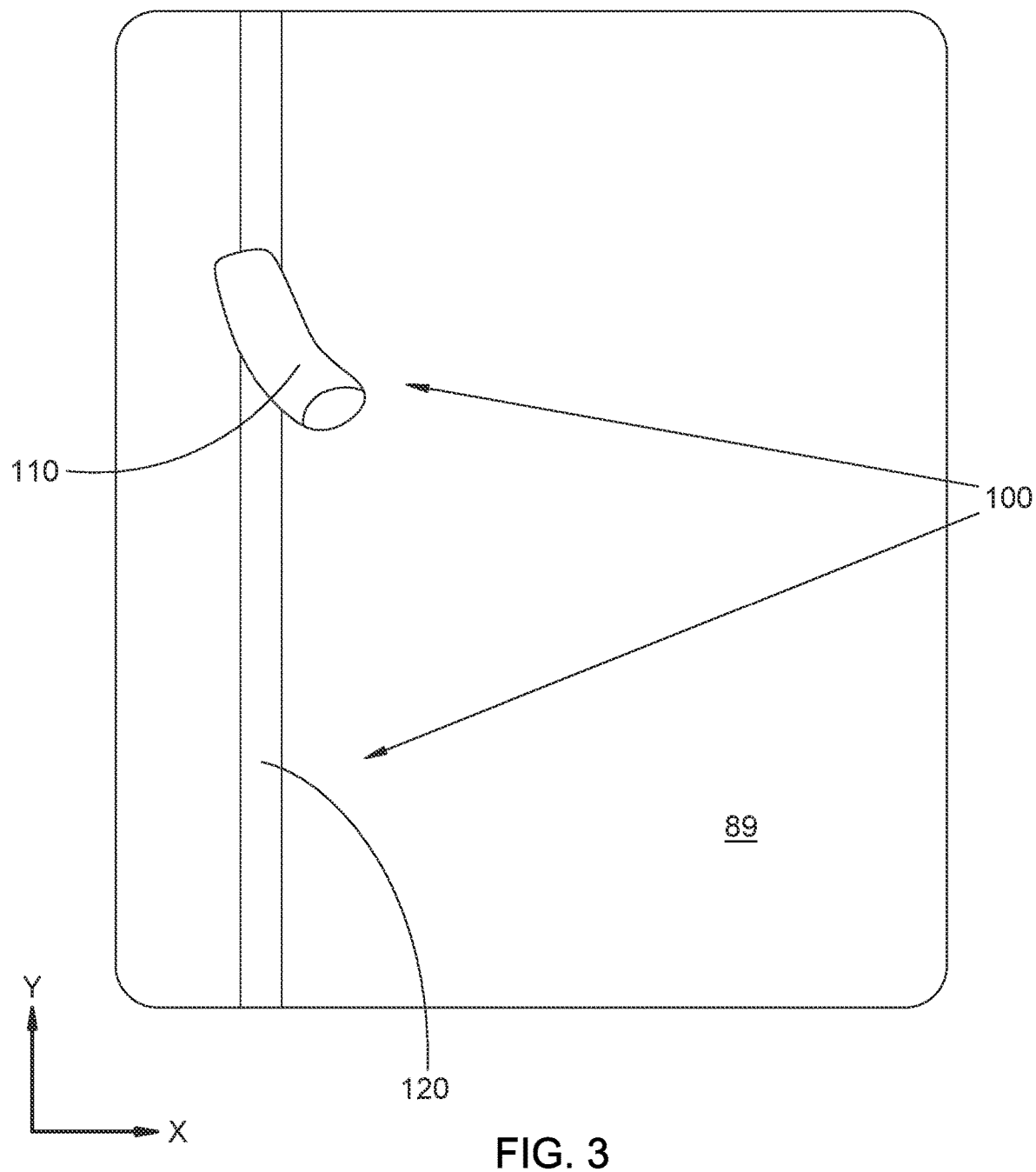
FIG. 3 illustrates schematically an example of a limb restraint having a longitudinal strap and being positioned for receiving a side-sleeper's arm.
Figure 4:
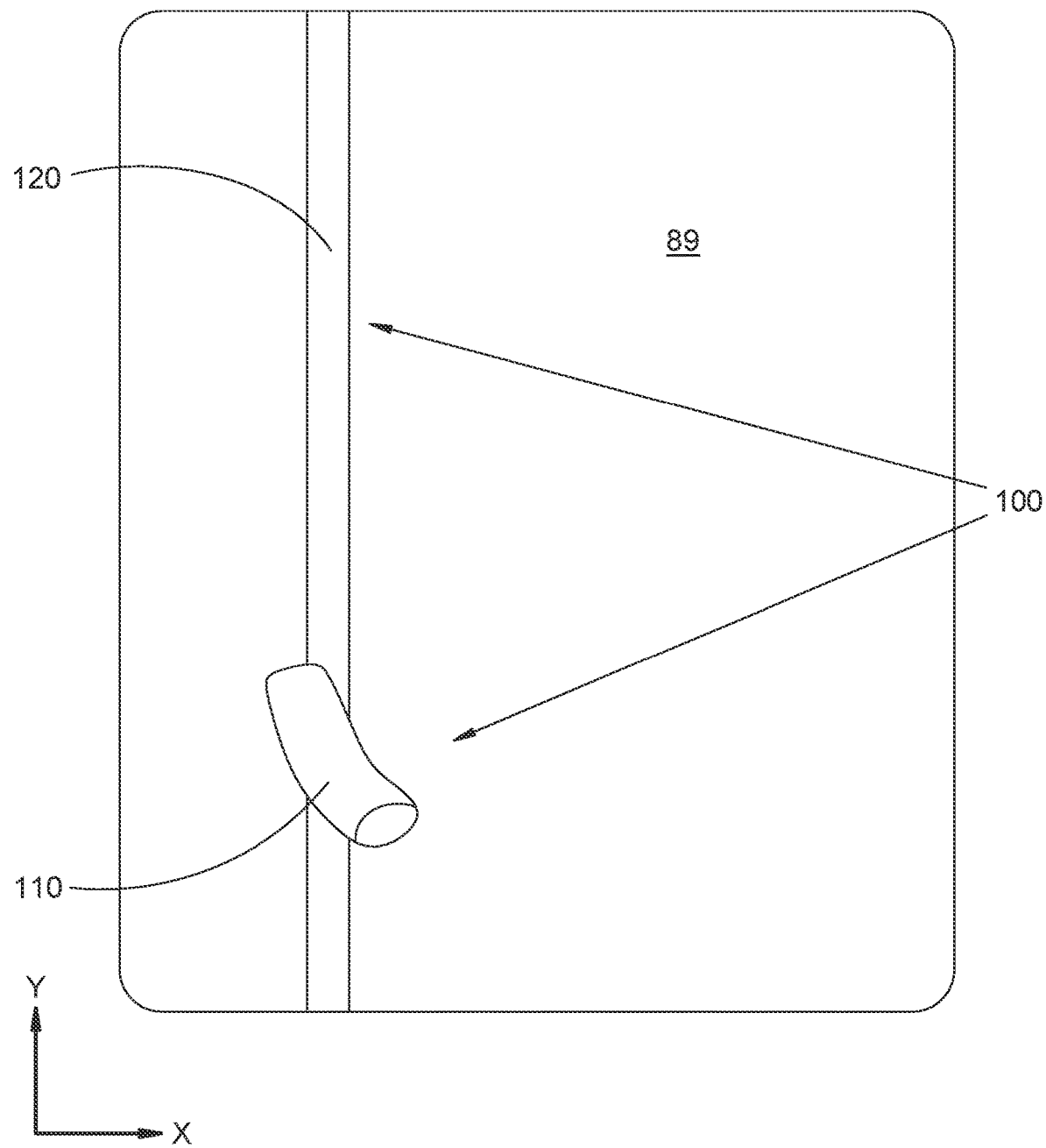
FIG. 4 illustrates schematically an example of a limb restraint having a longitudinal strap and being positioned for receiving a side-sleeper's leg.
Figure 5:
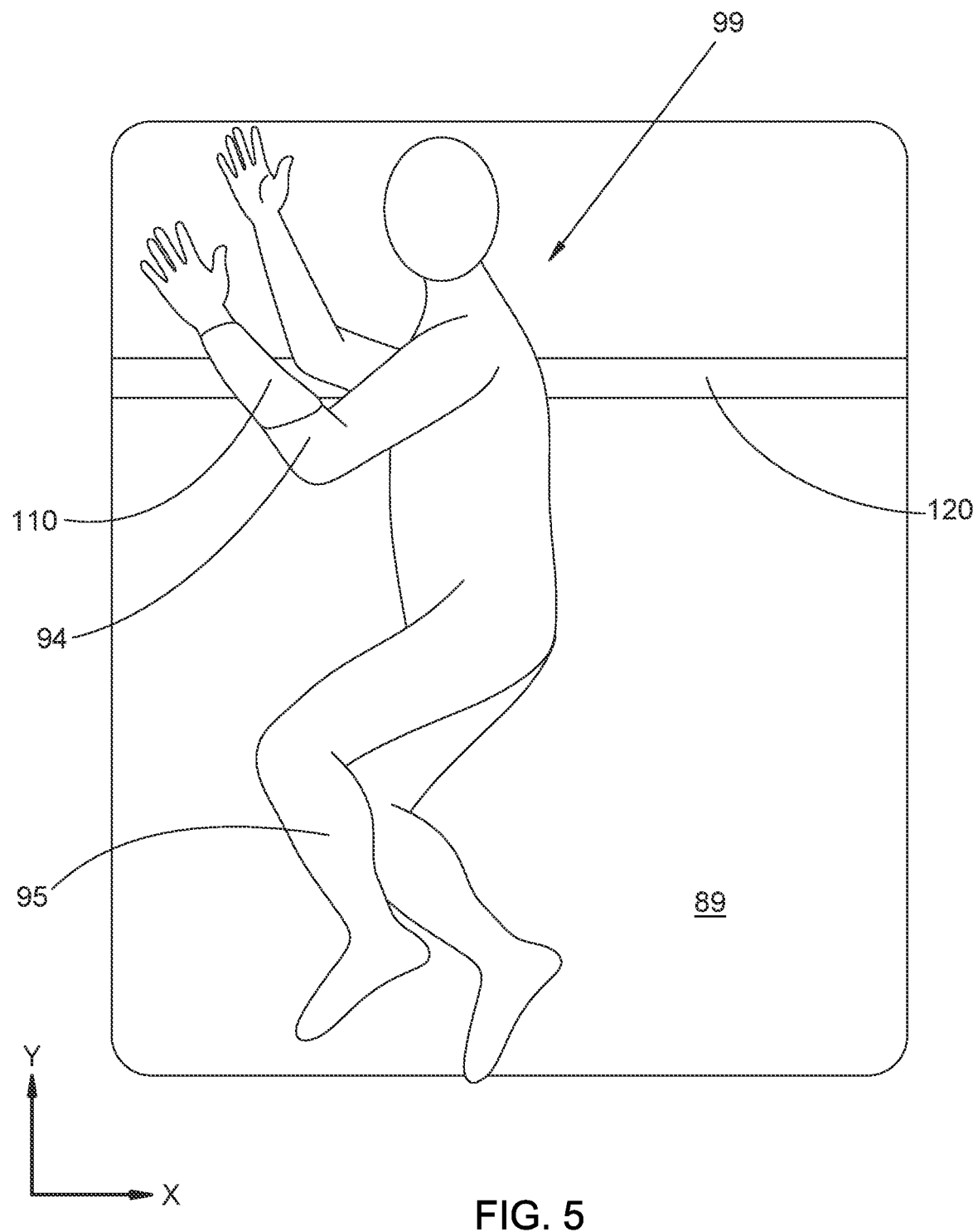
FIG. 5 illustrates schematically a side-sleeper using an example of a limb restraint having a transverse strap and restraining the side-sleeper's arm.
Figure 6:
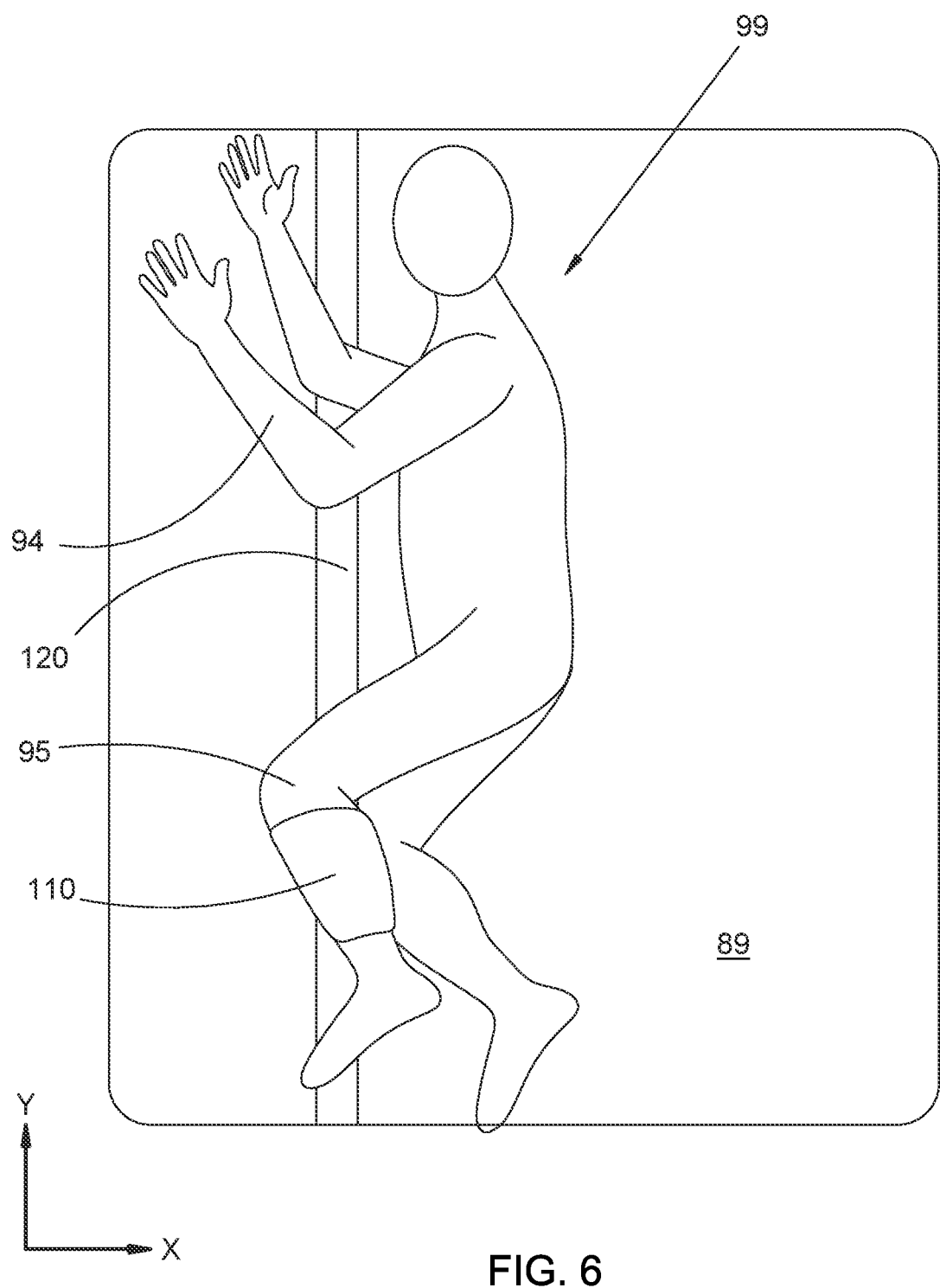
FIG. 6 illustrates schematically a side-sleeper using an example of a limb restraint having a longitudinal strap and restraining the side-sleeper's leg.

The embodiments depicted are shown only schematically; all features may not be shown in full detail or in proper proportion; for clarity certain features or structures may be exaggerated or diminished relative to others or omitted entirely; the drawings should not be regarded as being to scale unless explicitly indicated as being to scale. The embodiments shown are only examples and should not be construed as limiting the scope of the present disclosure or appended claims.

DETAILED DESCRIPTION

The following detailed description should be read with reference to the drawings, in which identical reference numbers refer to like elements throughout the different figures. The drawings, which are not necessarily to scale, depict selective examples and are not intended to limit the scope of the disclosed subject matter. The detailed description illustrates by way of example, not by way of limitation, the principles of the disclosed subject matter.

In the present disclosure, the term "sleeper" is used to identify a human being who sleeps at certain times; the term "sleeper" is used even while the person is preparing for bed and about to fall asleep, while the person is sleeping, or while the person awakes, either temporarily or after a sleep period. It is assumed herein that the bed is a flat or relatively flat surface on which a sleeper sleeps; a bed may be tilted or not, and powered or not, and may be also called by other terms, such as a cot, a couch or divan, or other suitable sleeping furniture. In the present disclosure, with a sleeper in a side-sleeping position, the side of the sleeper on the bottom, against a mattress or other sleep surface, shall be referred to as the downward side; the opposite side of the sleeper shall be referred to as the upward side. Accordingly, when a sleeper is sleeping on his or her right side, the sleeper's right side is the downward side and the sleeper's left side is the upward side; when a sleeper is sleeping on his or her left side, the sleeper's left side is the downward side and the sleeper's right side is the upward side.

It would be desirable to provide a limb restraint that attaches to both a sleeper and to a mattress or bedframe to keep the sleeper in a side-sleeping position (i.e., a lateral decubitus position or a lateral recumbent position). With suitable adjustment or arrangement, apparatus and methods disclosed herein can be employed for maintaining a sleeper in a side-sleeping position on the sleeper's right side or left side as needed.

A limb restraint 100 includes a flexible limb sleeve 110 and a strap 120; examples are shown in FIGS. 1-6. Flexible limb sleeve 110 is sized, shaped, and structurally arranged to permit a limb (arm 94 or leg 95) of sleeper 99 to be intentionally inserted into or removed from limb sleeve 110 while sleeper 99 is awake, but also to inhibit unintentional removal of limb 94 or 95 from limb sleeve 110 by sleeper 99 while sleeping. Strap 120 is structurally arranged to connect limb sleeve 110 to a mattress 89, or to a bedframe supporting mattress 89. Strap 120 connects limb sleeve 110 to mattress 89 or the bedframe so that limb sleeve 110 is in front of sleeper 99 while sleeping on the mattress in a side-sleeping position (e.g., as in FIG. 5 or FIG. 6). With sleeper 99 on mattress 89 in a side-sleeping position, and with an upward-side limb (arm 94 or leg 95) of sleeper 99 inserted into limb sleeve 110, limb restraint 100 maintains sleeper 99 in the side-sleeping position while asleep (e.g., as in FIGS. 5 and 6). Inserting a downward-side limb of sleeper 99 into limb sleeve 110 would not prevent sleeper 99, when in side-sleeping position, from rolling onto his or her back.

In some examples, limb sleeve 110 can be sized and positioned such that a sleeper's arm 94 is held by limb sleeve 110; in some such examples limb sleeve 110 extends from the sleeper's hand or wrist over some or all of the forearm toward the elbow. In some examples, limb sleeve 110 can be sized and positioned such that a sleeper's leg 95 is held by limb sleeve 110; in some such examples limb sleeve 110 extends from the sleeper's foot or ankle over some or all of the lower leg toward the knee. In the examples shown in the drawings, only arm 94 is received by limb sleeve 110 (as in FIG. 1, FIG. 3, or FIG. 5) or only leg 95 is received by limb sleeve 110 (as in FIG. 2, FIG. 4, or FIG. 6). The present disclosure also encompasses examples (not shown) wherein limb restraint 100 includes two limb sleeves 110, one positioned and arranged for receiving arm 94 and the other positioned and arranged for receiving leg 95. In some such examples the two limb sleeves 110 can be connected to mattress 89 or the bedframe by a single strap 120; in other such examples the two limb sleeves 110 can be connected to two separate straps 120.

In any of those examples (arm, leg, or both), if sleeper 99 begins to roll over onto his or her back, voluntarily or involuntarily while asleep, limb 94 or 95 (or both) secured by limb restraint 100 prevents such movement and keeps sleeper 99 in the side-sleeping position. The acts of securing limb restraint 100 to mattress 89 or the bedframe, inserting upward-side limb 94 or 95 (or both) of sleeper 99 into limb sleeve 110 (or limb sleeves 110), and positioning sleeper 99 in a side-sleeping position can be performed by sleeper 99 himself or herself, or by (or with the aid of) an assistant, such as a spouse, attendant, nurse, aide, or caregiver.

By keeping sleeper 99 in a side-sleeping position, snoring or positional sleep apnea or both can be reduced in at least some persons. By using limb restraint 100, a user can reduce instances of snoring or positional sleep apnea without resorting to other, more intrusive, uncomfortable, or expensive devices (e.g., CPAP, BiPAP, mandibular devices, or implantable devices).

Flexible limb sleeve 110 can be made of any suitably strong, suitably flexible material, and in some examples can be made of a textile or fabric, e.g., a cotton material or a polyester/spandex blend. In various examples the material of limb sleeve 110 can be, e.g., a breathable fabric, a washable fabric, a stretchable fabric, or a non-stretchable fabric. In some examples limb sleeve 110 can be tubular, and limb 94 or 95 can be inserted through the tubular structure or pulled out of the tubular structure. In some examples, limb sleeve 110 can be tapered, either regularly (i.e., frusto-conical) or non-regularly, such as to match a limb shape or average limb shape. In some examples limb sleeve 110 can be sufficiently stretchable to accommodate arms or legs of sleepers of a wide range of sizes; in other examples limb sleeves 110 of differing widths can be provided to accommodate arms or legs of sleepers of different sizes. In some examples, limb sleeve 110 can fit over arm 94 like a slightly snug shirt-sleeve. Similarly, examples of limb sleeve 110 suitable for a sleeper's leg 95 can fit over leg 95 like a section of slightly snug tights or leggings.

Structural features can allow intentional insertion and removal of limb 94 or 95 into or from limb sleeve 110 (with the sleeper awake) while inhibiting unintentional removal of limb 94 or 95 from limb sleeve 110 (when the sleeper is asleep). In some examples (including tubular examples) snugness or elasticity of limb sleeve 110 can be employed for that purpose. In some examples (including tubular examples) a cuff portion at an end of limb sleeve 110 can have a closure mechanism of a suitable type to permit passage of a hand or foot while open, but prevent removal of the hand or foot while closed. In some examples a suitable closure can secure limb sleeve 110 against limb 94 or 95; such a closure can in some examples facilitate size adjustments as well, even adjustments through a wide range of sizes. Examples employing a closure can include hook-and-loop attachment(s) (such as Velcro®), spring cord lock(s), snap(s), button(s), or zipper(s), or combinations thereof. Such a closure would not fully close limb sleeve 110 but rather would tighten it to secure limb sleeve 110 against limb 94 or 95.

A "strap" is often defined as having a thin, flattened cross-sectional shape, but strap 120 can have a suitable cross-sectional shape, albeit a flattened shape may be convenient for sleeper comfort. In some examples strap 120 can wrap entirely around mattress 89; in some of those examples strap 120 can surround a box spring or platform (if present) or a bedframe (if present). In some examples strap 120 can include a suitable closure, e.g., one or more hook-and-loop fasteners (such as Velcro®) or buckles. In other examples, strap 120 may have no closure but rather be fastened or manufactured in a loop of a desired size, with the ends (or one end and another point) permanently attached, such as by sewing or fabric welding; in such examples, it may be desired to use a suitable material, such as an elastic, and to size strap 120 so that it can loop around mattress 89. In some examples strap 120 can be adjustable to accommodate different sizes of mattress 89 or the bedframe. Strap 120 can be constructed from any suitably strong, suitably flexible material, e.g., nylon, cotton, plastic, leather, and so forth. Strap 120 can be a suitable width, e.g., between 2 and 12 inches wide.

In some examples strap 120 can be wrapped around mattress 89 or the bedframe in a transverse arrangement, i.e., spanning mattress 89 from one side to the other (parallel to the X-direction in the figures; as in FIGS. 1, 2, and 5); in such a transversely wrapped arrangement, the longitudinal position of strap 120 (i.e., the position between the head and foot of mattress 89) can be selected by choosing where to wrap strap 120. In some examples strap 120 can be wrapped around mattress 89 or the bedframe in a longitudinal arrangement, i.e., spanning mattress 89 from head to foot (parallel to the Y-direction in the figures; as in FIGS. 3, 4, and 6); in such a longitudinally wrapped arrangement, the transverse position of strap 120 (i.e., the position between the sides of mattress 89) can be selected by choosing where to wrap strap 120. Whether in transverse or longitudinal arrangements, strap 120 need not be precisely parallel to an edge of mattress 89. Rather, in some examples, strap 120 may be angled somewhat, which may add to sleeper comfort, and in such examples (not shown) strap 120 may be sized and structured to accommodate such angular adjustments. Even if angled somewhat, such angular examples can be considered transversely or longitudinally oriented, depending on whether strap 120 wraps around mattress 89 (or the bedframe) from head to foot or from side to side.

Instead of wrapping around mattress 89 (or other parts of the bed), in some examples the ends of strap 120 can be secured to the bedframe so that strap 120 spans only the top surface of mattress 89, either transversely or horizontally. In such examples strap 120 can be secured to the bedframe in a suitable way, e.g., by tying, or by loops formed from the ends of strap 120 using hook-and-loop fastener(s) (such as Velcro®), snap(s), button(s), or other suitable fastener(s). The transverse position of a longitudinally arranged strap 120, or the longitudinal position of a transversely arranged strap 120, can be selected as described above.

Figure 7:
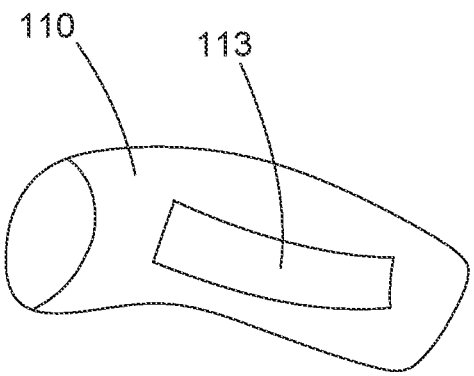
FIG. 7 illustrates schematically an example of a limb sleeve having a loop for engaging the strap.
Figure 8A:
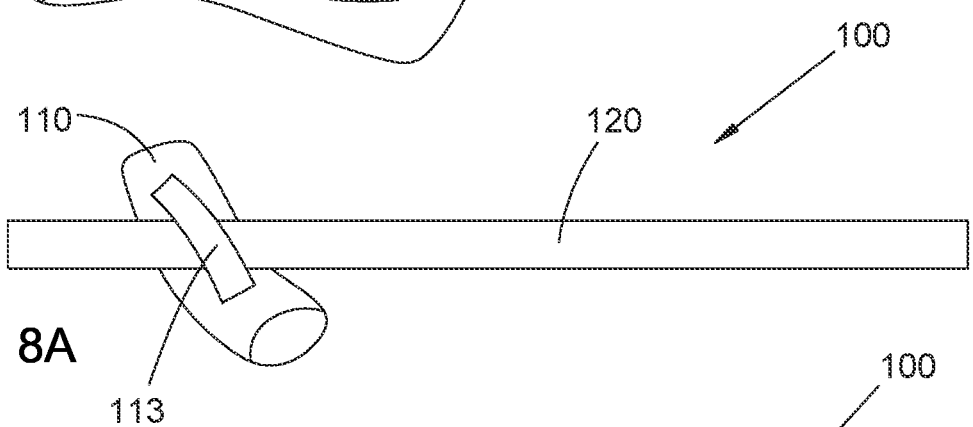
FIG. 8A and FIG. 8B illustrate movement along the strap of an example of a limb sleeve having a loop for engaging the strap.
Figure 8B:
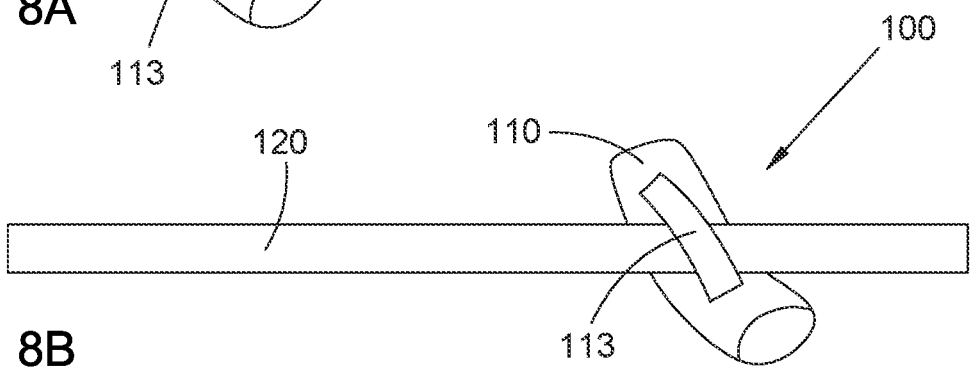

Strap 120 connects flexible sleeve 110 to mattress 89, to the bedframe, or to other portions of the bed. Limb sleeve 110 can be attached to or engaged with strap 120 in a suitable way. In some examples limb sleeve 110 can be slidably engaged with strap 120, which enables movement of limb sleeve 110 along strap 120 while being connected by strap 120 to mattress 89 or to the bed. Various slidable arrangements can be employed. In some examples (e.g., as in FIG. 7, in FIG. 8A and FIG. 8B, and in FIG. 9A and FIG. 9B) a loop 113 can be attached to the outer surface of the sleeve 110 in a suitable way, e.g., non-detachable (such as being sewn or fabric welded) or detachable (such as with hook-and-loop fastener(s) (e.g., Velcro®), snap(s), button(s), or zipper(s)). Loop 113 receives strap 120 therethrough; with limb sleeve 110 thus engaged with strap 120, limb sleeve 110 is connected to mattress 89 or the bed by strap 120 and can also move along strap 120 (illustrated schematically in FIG. 8A or FIG. 8B). Such a slidable arrangement, along with the variable placement of strap 120 as described above, can assist in placement of limb sleeve 110 at a wide array of locations on mattress 89, as sleeper 99 might desire. In particular, such flexibility of placement of limb sleeve 110 can enable sleeper 99 to assume a variety of side-sleeping positions, including choosing on which side to assume the side-sleeping position.

In some examples limb sleeve 110 can be attached to strap 120 at a fixed point on the strap. In some examples limb sleeve 110 can be non-detachable. In some examples limb sleeve 110 can be detachable from the fixed point on strap 120, such as for cleaning. In some examples, a detachable limb sleeve 110 can be re-attachable at a different fixed point on strap 120.

Figure 9A:
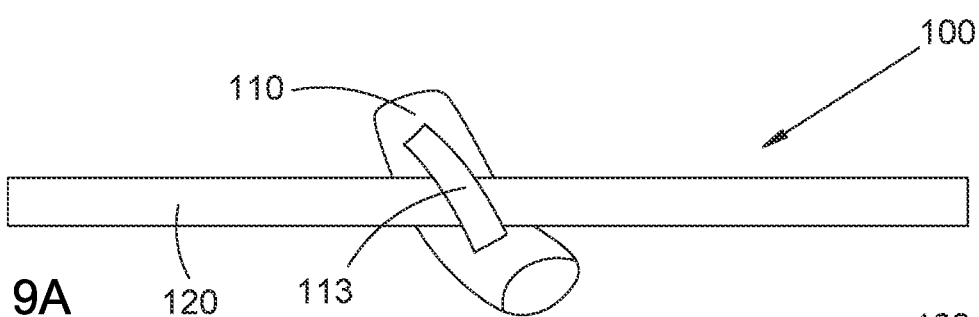
FIG. 9A and FIG. 9B illustrate rotation relative to the strap of an example of a limb sleeve having a loop for engaging the strap.
Figure 9B:
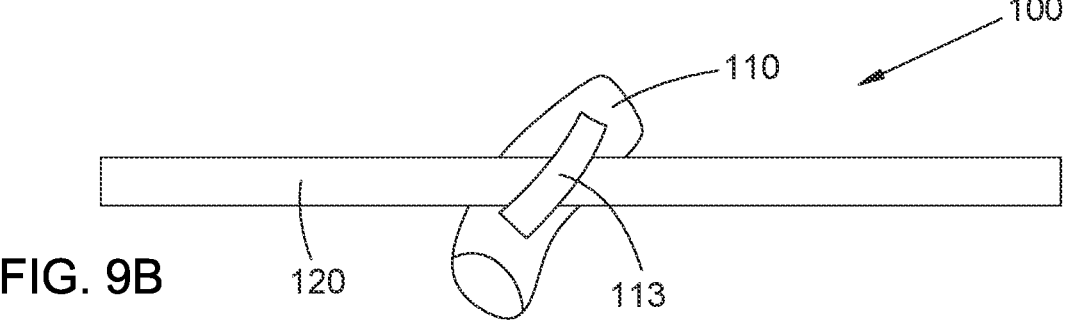

In some examples limb sleeve 110 can be rotatably engaged with strap 120 in a suitable way to enable rotation of limb sleeve 110 relative to strap 120 while being connected by strap 120 to mattress 89 or the bed (illustrated schematically in FIG. 9A and FIG. 9B). One example of such rotatable attachment of limb sleeve 110 to strap 120 includes loop 113 on limb sleeve 110, as described above. Another example (not shown) includes a round snap having two parts that can rotate with respect to one another. Whether or not there is sliding engagement as described above, loop 113 can be arranged so that limb sleeve 110 can rotate relative to strap 120. In other examples, limb sleeve 110 can be attached at a fixed angle relative to strap 120 between 0° and 180° (e.g., between 75° and 90°, or between 105° and 135°). Such fixed attachment can be non-detachable (e.g., sewn or fabric welded) or detachable/re-attachable (e.g., using a hook-and-loop fastener such as Velcro®, snap(s), button(s), or zipper(s)), as described above. Varying or selecting the angle between limb sleeve 110 and strap 120 enables accommodation of various side-sleeping positions, so that sleeper 99 can find a comfortable side-sleeping position. Such rotatable arrangements, along with the variable placement of strap 120 and limb sleeve 110 as described above, can assist in controlling the orientation or location of limb sleeve 110 to permit sleeper 99 to insert an upward-side limb of sleeper 99 into limb sleeve 110 in a comfortable fashion. However, rotatable arrangements or slidable arrangements are not considered necessary to accommodate an upward-side limb of sleeper 99, provided that sleeve 110 and strap 120 or suitably sized and oriented relative to one another and instructions guide users to insert an upward-side limb.

In addition to the preceding, the following example embodiments fall within the scope of the present disclosure or appended claims. Any given Example below that refers to multiple preceding Examples shall be understood to refer to only those preceding Examples with which the given Example is not inconsistent, and to exclude implicitly those preceding Examples with which the given Example is inconsistent.

Example 1. A method for maintaining a sleeper in a side-sleeping position, the method comprising: (a) securing to a mattress, or to a bedframe supporting the mattress, a limb restraint, the limb restraint including a flexible limb sleeve and a strap arranged to connect the limb sleeve to the mattress or bedframe, the limb restraint being secured so that the limb sleeve is in front of the sleeper while the sleeper is sleeping on the mattress in the side-sleeping position; (b) inserting an upward-side limb of the sleeper into the limb sleeve, the limb sleeve being sized, shaped, and structurally arranged (i) so as to permit the limb to be intentionally inserted into or removed from the sleeve by the sleeper while awake, and (ii) so as to inhibit unintentional removal of the limb from the sleeve by the sleeper while sleeping in the side-sleeping position.

Example 2. A limb restraint for maintaining a sleeper in a side-sleeping position, the limb restraint comprising: (a) a flexible limb sleeve that is sized, shaped, and structurally arranged (i) so as to permit a limb of the sleeper to be intentionally inserted into or removed from the sleeve by the sleeper while awake, and (ii) so as to inhibit unintentional removal of the limb from the sleeve by the sleeper while sleeping; and (b) a strap connected to the limb sleeve and couplable to a mattress, or to a bedframe supporting the mattress, wherein the connection between the strap and the limb sleeve is positioned so that (i) the limb sleeve is in front of the sleeper while sleeping on the mattress in the side-sleeping position, and (ii) the limb sleeve is positioned to receive an upward-side limb of the sleeper.

Example 3. The method of Example 1 or the apparatus of Example 2 wherein the upward-side limb of the sleeper inserted into the limb sleeve is a hand, wrist, or forearm of the sleeper.

Example 4. The method of Example 1 or the apparatus of Example 2 wherein the upward-side limb of the sleeper inserted into the limb sleeve is a foot, ankle, or lower leg of the sleeper.

Example 5. The method or apparatus of any one of Examples 1 through 4 wherein the strap is arranged to span the mattress along a longitudinal direction.

Example 6. The method or apparatus of any one of Examples 1 through 4 wherein the strap is arranged to span the mattress along a transverse direction.

Example 7. The method or apparatus of any one of Examples 1 through 6 wherein the limb sleeve is slidably engaged with the strap so as to enable movement of the limb sleeve along the strap while being connected by the strap to the mattress or bedframe.

Example 8. The method or apparatus of any one of Examples 1 through 6 wherein the limb sleeve is attached to the strap at a fixed point on the strap.

Example 9. The method or apparatus of Example 8 wherein the limb sleeve is detachable from the fixed point on the strap and re-attachable at a different fixed point on the strap.

Example 10. The method or apparatus of any one of Examples 1 through 9 wherein the limb sleeve is attached to the strap so as form an angle between 75° and 90° therebetween.

Example 11. The method or apparatus of any one of Examples 1 through 9 wherein the limb sleeve is attached to the strap so as form an angle between 105° and 135° therebetween.

Example 12. The method or apparatus of any one of Examples 1 through 11 wherein the limb sleeve is rotatably engaged with the strap so as to enable rotation of the sleeve relative to the strap.

This disclosure is illustrative and not limiting. Further modifications will be apparent to one skilled in the art in light of this disclosure and are intended to fall within the scope of the present disclosure or appended claims. It is intended that equivalents of the disclosed example embodiments and methods, or modifications thereof, shall fall within the scope of the present disclosure or appended claims.

In the foregoing Detailed Description, including the drawings, various features may be grouped together in several example embodiments for the purpose of streamlining the disclosure. This method of disclosure is not to be interpreted as reflecting an intention that any claimed embodiment requires more features than are expressly recited in the corresponding claim or that any recited feature or features are necessary. Rather, as the appended claims reflect, inventive subject matter may lie in less than all features of a single disclosed example embodiment. Therefore, the present disclosure shall be construed as disclosing any embodiment having any suitable subset of one or more features shown, described, or claimed in the present disclosure—including those subsets that may not be separately discussed herein in that specific combination. A "suitable" subset of features includes only features that are neither incompatible nor mutually exclusive with respect to any other feature of that subset. Accordingly, the appended claims are hereby incorporated in their entirety into the Detailed Description, with each claim standing on its own as a separate disclosed embodiment. In addition, each of the appended dependent claims shall be interpreted, only for purposes of disclosure by said incorporation of the claims into the Detailed Description, as if written in multiple dependent form and dependent upon all other claims with which it is not inconsistent. It should be further noted that the cumulative scope of the appended claims can, but does not necessarily, encompass the whole of the subject matter disclosed in the present application.

The following interpretations shall apply for purposes of the present disclosure and appended claims. The words "comprising," "including," "having," and variants thereof, wherever they appear, shall be construed as open-ended terminology, with the same meaning as if a phrase such as "at least" were appended after each instance thereof, unless explicitly stated otherwise. The article "a" shall be interpreted as "one or more" unless "only one," "a single," or other similar limitation is stated explicitly or is implicit in the particular context; similarly, the article "the" shall be interpreted as "one or more of the" unless "only one of the," "a single one of the," or other similar limitation is stated explicitly or is necessary in the particular context. The conjunction "or" is to be construed inclusively unless: (i) it is explicitly stated otherwise, e.g., by use of "either . . . or," "only one of," or similar language; or (ii) two or more of the listed alternatives are understood or disclosed (necessarily or explicitly) to be incompatible or mutually exclusive within the particular context. In that latter case, "or" would be understood to encompass only those combinations involving non-mutually-exclusive alternatives. In one example, each of "a dog or a cat," "one or more of a dog or a cat," and "one or more dogs or cats" would be interpreted as one or more dogs without any cats, or one or more cats without any dogs, or one or more of each.

For purposes of the present disclosure and appended claims, when a numerical quantity is recited (with or without terms such as "about," "about equal to," "substantially equal to," "greater than about," "less than about," and so forth), standard conventions pertaining to measurement precision, rounding error, and significant digits shall apply, unless a differing interpretation is explicitly set forth, or if a differing interpretation is inherent (e.g., some small integer quantities). For null quantities described by phrases such as "equal to zero," "absent," "eliminated," "negligible," "prevented," and so forth (with or without terms such as "about," "substantially," and so forth), each such phrase shall denote the case wherein the quantity in question has been reduced or diminished to such an extent that, for practical purposes in the context of the intended operation or use of the disclosed or claimed apparatus or method, the overall behavior or performance of the apparatus or method does not differ from that which would have occurred had the null quantity in fact been completely removed, exactly equal to zero, or otherwise exactly nulled. Terms such as "parallel," "perpendicular," "orthogonal," "flush," "aligned," and so forth shall be similarly interpreted (with or without terms such as "about," "substantially," and so forth).

For purposes of the present disclosure and appended claims, any labelling of elements, steps, limitations, or other portions of an embodiment, example, or claim (e.g., first, second, third, etc., (a), (b), (c), etc., or (i), (ii), (iii), etc.) is only for purposes of clarity, and shall not be construed as implying any sort of ordering or precedence of the portions so labelled. If any such ordering or precedence is intended, it will be explicitly recited in the embodiment, example, or claim or, in some instances, it will be inherent based on the specific content of the embodiment, example, or claim. In the appended claims, if the provisions of 35 USC § 112(f) are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC § 112(f) are not intended to be invoked for that claim.

If any one or more disclosures are incorporated herein by reference and such incorporated disclosures conflict in part or whole with, or differ in scope from, the present disclosure, then to the extent of conflict, broader disclosure, or broader definition of terms, the present disclosure controls. If such incorporated disclosures conflict in part or whole with one another, then to the extent of conflict, the later-dated disclosure controls.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. A method for maintaining a sleeper in a side-sleeping position, the method comprising:
   (a) securing to a mattress, or to a bedframe supporting the mattress, a limb restraint, the limb restraint including: (i) a flexible limb sleeve, and (ii) a strap arranged to connect the limb sleeve to the mattress or bedframe, wherein the limb restraint is secured so that the limb sleeve is positioned against a top surface of the mattress in front of the sleeper while the sleeper is sleeping on the mattress in the side-sleeping position;
   (b) inserting an upward-side limb of the sleeper into the limb sleeve so as to hold the upward-side limb against the top surface of the mattress, the limb sleeve being sized, shaped, and structurally arranged (i) so as to permit the limb to be intentionally inserted into or removed from the sleeve by the sleeper while awake, and (ii) so as to inhibit unintentional removal of the limb from the sleeve by the sleeper while sleeping in the side-sleeping position.

2. The method of claim 1 wherein the upward-side limb of the sleeper inserted into the limb sleeve is a hand, wrist, or forearm of the sleeper.

3. The method of claim 1 wherein the upward-side limb of the sleeper inserted into the limb sleeve is a foot, ankle, or lower leg of the sleeper.

4. The method of claim 1 wherein the strap is arranged to span the mattress along a longitudinal direction.

5. The method of claim 1 wherein the strap is arranged to span the mattress along a transverse direction.

6. The method of claim 1 wherein the limb sleeve is slidably engaged with the strap so as to enable movement of the limb sleeve along the strap while the limb sleeve remains positioned against the top surface of the mattress.

7. The method of claim 1 wherein the limb sleeve is attached to the strap at a fixed point on the strap.

8. The method of claim 7 wherein the limb sleeve is detachable from the fixed point on the strap and re-attachable at a different fixed point on the strap positioned against the top surface of the mattress.

9. The method of claim 1 wherein the limb sleeve is attached to the strap so as form an angle between 75° and 90° therebetween, in a plane parallel to the top surface of the mattress.

10. The method of claim 1 wherein the limb sleeve is attached to the strap so as form an angle between 105° and 135° therebetween, in a plane parallel to the top surface of the mattress.

11. The method of claim 1 wherein the limb sleeve is rotatably engaged with the strap so as to enable rotation of the sleeve relative to the strap in a plane parallel to the top surface of the mattress.

12. A limb restraint for maintaining a sleeper in a side-sleeping position, the limb restraint comprising:
   (a) a flexible limb sleeve that is sized, shaped, and structurally arranged (i) so as to permit a limb of the sleeper to be intentionally inserted into or removed from the sleeve by the sleeper while awake, and (ii) so as to inhibit unintentional removal of the limb from the sleeve by the sleeper while sleeping; and
   (b) a strap connected to the limb sleeve and couplable to a mattress, or to a bedframe supporting the mattress, wherein the connection between the strap and the limb sleeve is positioned so that (i) the limb sleeve is positioned against a top surface of the mattress in front of the sleeper while sleeping on the mattress in the side-sleeping position, and (ii) the limb sleeve is positioned to receive an upward-side limb of the sleeper and to hold the upward-side limb against the top surface of the mattress,
   (c) the limb sleeve being rotatably engaged with the strap so as to enable rotation of the sleeve relative to the strap in a plane parallel to the top surface of the mattress.

13. The limb restraint of claim 12 wherein the strap is arranged to span the mattress along a longitudinal direction.

14. The limb restraint of claim 12 wherein the strap is arranged to span the mattress along a transverse direction.

15. The limb restraint of claim 12 wherein the limb sleeve is slidably engaged with the strap so as to enable movement of the limb sleeve along the strap while the limb sleeve remains positioned against the top surface of the mattress.

16. The limb restraint of claim 12 wherein the limb sleeve is attached to the strap at a fixed point on the strap.

17. The limb restraint of claim 16 wherein the limb sleeve is detachable from the fixed point on the strap and re-attachable at a different fixed point on the strap positioned against the top surface of the mattress.

18. The limb restraint of claim 12 wherein the limb sleeve is attached to the strap so as form an angle between 75° and 90° therebetween, in a plane parallel to the top surface of the mattress.

19. The limb restraint of claim 12 wherein the limb sleeve is attached to the strap so as form an angle between 105° and 135° therebetween, in a plane parallel to the top surface of the mattress.

* * * * *